(12) United States Patent
Ryan

(10) Patent No.: US 6,653,137 B2
(45) Date of Patent: Nov. 25, 2003

(54) HEMATOLOGY REFERENCE CONTROL

(75) Inventor: Wayne L. Ryan, Omaha, NE (US)

(73) Assignee: Streck Laboratories Inc., La Vista, NE (US)

(*) Notice: Subject to any disclaimer, the term of this patent is extended or adjusted under 35 U.S.C. 154(b) by 38 days.

(21) Appl. No.: 10/007,519

(22) Filed: Dec. 3, 2001

(65) Prior Publication Data

US 2003/0104629 A1 Jun. 5, 2003

(51) Int. Cl.$^7$ ............................................ G01N 31/00
(52) U.S. Cl. .................. 436/10; 436/8; 436/63; 436/164; 422/73; 422/82.05; 435/2
(58) Field of Search ................ 436/8, 10, 17, 436/18, 63, 164, 174; 422/73, 82.05; 435/2

(56) References Cited

U.S. PATENT DOCUMENTS

| | | |
|---|---|---|
| 3,558,522 A | 1/1971 | Louderback et al. |
| 3,574,137 A | 4/1971 | DeCasperis et al. |
| 3,607,783 A | 9/1971 | Tata |
| 3,640,896 A | 2/1972 | DeCasperis |
| 3,873,467 A | 3/1975 | Hunt |
| 4,099,917 A | 7/1978 | Kim |
| 4,160,644 A | 7/1979 | Ryan |
| 4,179,398 A | 12/1979 | Hunt |
| 4,198,206 A | 4/1980 | Ryan |
| 4,219,440 A | 8/1980 | Runck et al. |
| 4,264,470 A | 4/1981 | Chastain, Jr. et al. |
| 4,299,726 A | 11/1981 | Crews et al. |
| 4,324,686 A | 4/1982 | Mundschenk |
| 4,324,687 A | 4/1982 | Louderback et al. |
| 4,358,394 A | 11/1982 | Crews et al. |
| 4,389,490 A | 6/1983 | Crews et al. |
| 4,390,632 A | 6/1983 | Carter, II |
| 4,425,334 A | 1/1984 | Hunt |
| 4,436,821 A | 3/1984 | Ryan |
| 4,579,824 A | 4/1986 | Louderback et al. |
| 4,698,312 A | 10/1987 | Wong et al. |
| 4,704,364 A | 11/1987 | Carver et al. |
| 4,711,852 A | 12/1987 | Jacobson et al. |
| 4,745,071 A | 5/1988 | Lapicola et al. |
| 4,751,179 A | 6/1988 | Ledis et al. |
| 4,777,139 A | 10/1988 | Wong et al. |
| 5,008,021 A | 4/1991 | Conner et al. |
| 5,008,201 A | 4/1991 | Ryan |
| 5,196,182 A | 3/1993 | Ryan |
| 5,262,327 A | 11/1993 | Ryan |
| 5,270,208 A | 12/1993 | Ryan |
| 5,320,964 A | 6/1994 | Young et al. |
| 5,380,664 A | 1/1995 | Carver et al. |
| 5,389,664 A | 2/1995 | Baile et al. |
| 5,432,089 A | 7/1995 | Ryan et al. |
| 5,459,073 A | 10/1995 | Ryan |
| 5,460,797 A | 10/1995 | Ryan |
| 5,492,833 A | 2/1996 | Rodriguez et al. |
| 5,512,485 A | 4/1996 | Young et al. |
| 5,529,933 A | 6/1996 | Young et al. |
| 5,616,501 A | 4/1997 | Rodriguez et al. |
| 5,672,474 A | 9/1997 | Ryan |
| 5,677,145 A | 10/1997 | Ryan |
| 5,731,205 A | 3/1998 | Ryan |
| 5,736,402 A | 4/1998 | Francis et al. |
| 5,811,099 A | 9/1998 | Ryan |
| 5,811,303 A | 9/1998 | Ryan |
| 5,849,517 A | 12/1998 | Ryan |
| 5,858,789 A | 1/1999 | Francis et al. |
| 5,858,790 A | 1/1999 | Kim et al. |
| 5,874,310 A | 2/1999 | Li et al. |
| 5,874,311 A | 2/1999 | Li et al. |
| 5,888,790 A | 3/1999 | Cahoon et al. |
| 5,917,584 A | 6/1999 | Li et al. |
| 5,939,326 A | 8/1999 | Chupp et al. |
| 5,945,340 A | 8/1999 | Francis et al. |
| 5,981,282 A | 11/1999 | Ryan |
| 5,994,139 A | 11/1999 | Jacobs et al. |
| 6,060,322 A | 5/2000 | Horton et al. |
| 6,074,879 A | 6/2000 | Zelmanovic et al. |
| 6,197,593 B1 * | 3/2001 | Deka et al. .................. 436/63 |
| 6,200,500 B1 | 3/2001 | Ryan |
| 6,221,668 B1 | 4/2001 | Ryan et al. |
| 6,228,652 B1 | 5/2001 | Rodriguez et al. |
| 6,232,125 B1 | 5/2001 | Deka et al. |
| 6,362,003 B1 | 3/2002 | Young et al. |
| 6,399,388 B1 * | 6/2002 | Ryan et al. .................. 436/8 |
| 6,403,377 B1 * | 6/2002 | Ryan et al. .................. 436/8 |
| 6,406,915 B2 * | 6/2002 | Ryan et al. .................. 436/10 |
| 6,448,085 B1 * | 9/2002 | Wang et al. .................. 436/10 |
| 6,472,215 B1 * | 10/2002 | Huo et al. .................... 436/10 |

FOREIGN PATENT DOCUMENTS

| | | | |
|---|---|---|---|
| WO | WO 93/17329 | 3/1993 | |
| WO | WO 93/17330 | 3/1993 | |
| WO | WO 01/14872 | 3/2001 | .......... G01N/31/00 |

OTHER PUBLICATIONS

International Search Report for PCT Application No. PCT/US02/31718 dated Mar. 20, 2003.

Greenfield, et al., "Inhibition of Red Cell Membrane Lipid Peroxidation by Sulfasalazine and 5–Aminosalicylic Acid," Gut, pp. 1156–1159, (1991).

Lombarts, et al., "A Stable Human–Platelet–White Blood Cell Control for the Coulter Model S–Plus II," Clinica. Chimica. Acta., pp. 95–102, (1982).

Nergre–Salvayre, et al., "Protective Effect of a–Tocopherol, Ascorbic Acid and Rutin against Peroxidative Stress Induced by Oxidized Lipoproteins on Lymphoid Cell Lines," Biochem. Pharmacol., p. 450–453, (1991).

Sorette, et al., "Improved Isolation of Normal Human Reticulocytes via Exploitation of Chloride–Dependent Potassium Transport," Blood, vol. 80 (No. 1), P. 249–254, (Jul. 1, 1992).

Lombarts, et al. "A White Blood Cell Control for Long–Term Stability," Clinica. Chimica, Acta, 129:79–83 (1983).

\* cited by examiner

Primary Examiner—Maureen M. Wallenhorst
(74) Attorney, Agent, or Firm—Howrey Simon Arnold & White LLP

(57) ABSTRACT

An improved control for a hematology analyzer. In one embodiment, blood cells are treated for permitting the cells to simulate nucleated red blood cells for detection or analysis by the hematology analyzer.

14 Claims, No Drawings

HEMATOLOGY REFERENCE CONTROL

TECHNICAL FIELD

This invention relates generally to an improved method of making a hematology control composition, improved compositions, and their use in an automated or semi-automated hematology analyzer.

BACKGROUND

The proliferation of semi-automated and automated hematology instruments in recent years and the increased regulation of clinical laboratories has placed an increasing demand for high performance, long-term stable reference controls. Certain instruments characterize a sample of blood by detecting the impedance or light scatter or radiofrequency characteristics of cells in a sample. It has become especially popular to use these instruments for differentiating cells relative to each other, as well as for other flow cytometry techniques.

In both U.S. Pat. Nos. 6,187,590 and 5,858,790 (both incorporated by reference) the patentee identifies examples of certain of these instruments, including the ABBOTT CELL-DYN® 4000 Analyzer and the STKS® Analyzer from Beckman Coulter. In the latter patents, differences in the modes of detection of the respective instruments are emphasized as determinative of whether a particular control may properly function in the instrument. The differences are emphasized with particular reference to a control including a nucleated red blood cell component prepared from mammalian nucleated blood cells or avian or fish erythrocytes. The control disclosed is intended specifically for use in a multi-angle light scatter hematology analyzer, such as a CELL DYN® Analyzers. The nucleated red blood cell component is made by stripping a membrane from a nucleated cell.

It would be particularly attractive to provide a control including a simulated nucleated red blood cell component, wherein after preparation the nucleus remains at least partially, if not substantially wholly encapsulated with a membrane, and especially the natural membrane of the cell; thus also rendering the control sensitive to components of the instrument system (e.g., lysing agent, stain or dye, or the like). It would also be attractive to have a simulated nucleated red blood cell component that is useful in a control for any or all of instruments that measure hematological parameters by (for instance) light scatter, radiofrequency or electrical impedance.

SUMMARY OF THE INVENTION

The present invention meets the above needs by providing an improved control composition, and method of making and using the same.

In a particularly preferred embodiment a blood cell is provided for simulating a nucleated red blood cell. When provided, the blood cell has a nucleus and cytoplasm enclosed by a membrane. Cytoplasm is optionally removed from within the membrane and the membrane is handled for preserving it substantially intact at least partially encapsulating the nucleus. The resulting cell form is suspended in a suitable suspension medium and is capable of functioning as a simulated nucleated red blood cell.

In another embodiment, the resulting cell form is incorporated into a multi-parameter hematology control, and particularly one that includes a white blood cell component, prepared from red or white blood cells, adapted for simulating at least three, and more preferably five subpopulations of white blood cells.

In another embodiment, the white blood cell component is prepared from a sample of human whole blood in which white blood cells are fixed prior to lysing of the red blood cells from the whole blood. After red blood cell lysis, the white blood cells are again fixed for a period of at least about 1 hour, and more preferably about 4 to about 5 hours.

In another embodiment, compositions in accordance with the above are employed in a hematology analyzer as a reference control that detects blood cell characteristics on the basis of light scatter, electrical impedance, radiofrequency or a mixture thereof.

DETAILED DESCRIPTION OF PREFERRED EMBODIMENT

Blood Cell Source

One object of the present invention, as gathered from the foregoing, is to provide a component for a hematology reference control that simulates nucleated red blood cells of human blood. In this regard, the simulation does not necessarily mean that cells be chemically similar to the intended corresponding human cells. Rather, the desired simulation is in a characteristic that would be detected by an instrument suitable for analysis of such cells. For example, by way of summary, an instrument might detect the presence or amount of a particular cell by measuring one or more of light scatter, impedence, radiofrequency response or some other physical response or lack thereof to an applied stimulus.

Thus, as is well known in the art pertaining to blood cell analogs, as exemplified in a number of teachings spanning the past few decades, such as (without limitation) U.S. Pat. Nos. 3,574,137; 3,640,896; 3,873,467; 4,219,440; 4,704,364; 5,207,208; 5,262,327; 5,320,964; 5,389,664; 5,994,139; 6,187,590; 6,187,590 or the like (all of which are expressly incorporated by reference), the simulated blood cell component need not originate from a human blood cell. In fact, though human blood cells may be suitably employed in the present invention for any of the particular components, a preferred component for simulating a blood cell will be one that is derived from a blood cell other than a human blood cell.

In the context of one aspect of the present invention, by way of illustration, and though not intended as limiting, examples of sources of a cell component for simulating a human nucleated red blood cell include reptile nucleated blood cells, avian nucleated blood cells, fish nucleated blood cells or the like. Other mammalian blood cells may be employed as well, such as bovine cells, porcine cells, goat cells or otherwise. In a particularly preferred embodiment, the reptilian source of a nucleated blood cell is an alligator, the fish source is a salmon and the avian source is a turkey or chicken. Most preferably, the source of blood cell is an alligator, a salmon or a mixture thereof. It should be appreciated from the above that the source of the cell component for simulating a human nucleated red blood cell need not be a red blood cell, but may indeed be a nucleated white blood cell or other cell.

Starting materials for providing these components are widely available and preferably they are provided in a suitable suspension. For example, the starting material for a cell for simulating a human nucleated red blood cell may be suitably supplied in whole blood form or in a suspension form or otherwise in a suitable handling medium, (e.g., without limitation, a liquid or gel medium). Such medium preferably includes a suitable amount of an anti-coagulant, and may include other ingredients for stabilizing the cells during storage, transport and handling.

Early Stage Cell Preparation

For preparing nucleated red blood cells in accordance with the present invention, upon providing cells from a suitable source, the cells are treated as desired for removing any of the handling medium and for subsequent processing for forming a simulated human nucleated red blood cell. In one preferred embodiment, this can be accomplished by simply washing the cells with a suitable solution, preferably a buffered solution and still more preferably an isotonic wash solution, such as that described (without limitation) in further detail herein, under the heading "Isotonic Wash Solution".

This treatment step may be done below, at or above room temperature, but preferably under conditions for substantially maintaining the integrity of the nucleus of the cell and a major portion of the cell membrane.

Lysis of Nucleated Blood Cell

In one particularly preferred embodiment of the present invention, though not in every embodiment, lysis is performed upon the nucleated blood cell for permitting cytoplasm from within the cell membrane to escape through the membrane. It is preferred, in these instances, that the membrane remain at least partially surrounding the remaining nucleus. Lysis therefore preferably is a controlled lysis by which the membrane is permeated or otherwise penetrated for permitting the cytoplasm to escape, but still maintaining a sufficiently rigid structure for at least partially, if not substantially entirely, surrounding the remaining nucleus. Further, the lysis is sufficient for permitting a stain or dye to enter in later processing steps.

Any suitable lysing agent may be employed in its art-disclosed amount. By way of illustration a solution including about 3 to about 20, and more preferably about 5 to about 10 mg percent by weight saponin may be employed (wherein mg % refers to mg per 100 ml). Other lysing agents may be employed such as alcohols (e.g. methanol), a surfactant (e.g., sodium dodecyl sulfate or a cationic surfactant such as Triton X-100™), or those disclosed in U.S. Pat. Nos. 5,858,790 and 6,187,590.

In another embodiment, as illustrated in the Examples section herein, the present step of lysing is omitted entirely.

Later Stage Fixing of Cells

The cells for simulating nucleated red blood cells of the present invention may optionally be fixed in a later stage fixing step (e.g., after any optional step of lysing, or prior to admixing the cells into the medium for forming the resulting control) for substantially preserving the morphology and size of the cells. Any suitable fixative technique may be employed, such as by contact with a fixative agent, heating or a combination thereof.

The fixative is contacted with the cells for a time sufficient for substantially preserving cell morphology and size of the cells for at least about 2 weeks and more preferably at least about 45 days, and still more preferably at least about 75 days. The time may vary with factors such as the concentration of cells to fixative agent, the strength of the fixative or the like. However, it is preferred that fixing is accomplished over a duration of at least about 2 hours; more preferably at least about 12 hours; still more preferably at least bout 24 hours; even still more preferably at least about 48 hours; and even still more preferably at least about 96 hours. At higher temperatures, these times may be shorter.

Fixing may occur with the fixative agent at, below or above room temperature. In a highly preferred embodiment it occurs at about room temperature.

The fixative agent may be any suitable art disclosed fixative, including but not limited to those including an aldehyde, oxazolidine, alcohol, cyclic urea, or the like. Examples of particularly preferred fixatives include, without limitation, formaldehyde, glutaraldehyde, diazolidinyl urea (DU), imidazolidinyl urea (IDU), dimethylol urea, dimethylol-5,5-dimethylhydantoin, 2-bromo-2-nitropropane-1,3-diol; quaternary adamantine; -hydroxymethyl-1-aza3,7-dioxabicyclo (3.3.0)octane and 5-hydroxymethyl-1-aza-3,7-dioxabicyclo (3.3.0)octane and 5-hydroxypoly-methyleneoxy-methyl-1-aza-3,7-dioxabicyclo (3.3.0)octane, sodium hydroxymethyl glycinate, and mixtures thereof; and or the like.

Other fixatives may be used, such as those disclosed in U.S. Pat. Nos. 5,196,182; 5,262,327; 5,460,797; 5,811,099; 5,849,517; 6,221,668, and 5,529,933; 6,187,590; 6,187,590, all of which are hereby incorporated by reference. As will be appreciated from the above, if desired, the fixative may be selected for preserving one or more of the surface antigens present on the blood cells, for permitting stain or dyeing of the blood cells, or for enabling some other treatment of the cells before or during analysis by a hematology instrument.

Preferably the volume concentration ratios of fixative to cell suspension ranges from about 1:100 to about 100:1, more preferably about 1:20 to about 20:1, and still more preferably it is about 1:10 to about 10:1. One highly preferred example of a ratio is about 1:10.

Isotonic Wash Solution

As indicated in the above, the present invention makes use of a suitable isotonic wash solution in various steps of the washing, fixing or other handling of the blood cells for making a simulated nucleated red blood cell component or a control. Any suitable solution may be employed. Preferably, the solution will have a pH ranging from about 7.0 to about 7.8, and will have an osmolarity ranging from about 270 to about 340. Preferably the solution will include at least one or more, more preferably two or more, still more preferably three or more, and still more preferably four or more and still even more preferably all of the following ingredients:

1) a fungicide;

2) an antimicrobial;

3) a surfactant;

4) a buffer;

5) a metal chelating agent;

6) a cell nutrient; or 7) an agent for maintaining tonicity.

Though other quantitative ranges may be employed, in one preferred embodiment, at least a buffer, a surfactant, a metal chelating agent and an agent for maintaining tonicity is employed. By way of example, for such an embodiment the relative amounts of the above respective ingredients may fall within the following (expressed in parts by weight):

1) a fungicide up to about 5 parts;

2) an antimicrobial up to about 5 parts;

3) a surfactant in about 5 to about 20 parts;

4) a buffer in about 5 to about 30 parts;

5) a metal chelating agent in about 25 to about 50 parts;

6) a cell nutrient up to about 5 parts; and 7) an agent for maintaining tonicity in about 15 to about 35 parts.

Of course, other ingredients may also be employed in their art-disclosed quantities, such as (without limitation) that described in U.S. Pat. Nos. 5,858,790 or 6,187,590, hereby incorporated by reference.

Optionally, though certain of the above may already perform such functions, the solution may also include one or more agents that function as a hemolysis inhibitor, an aggregating agent, cell size, shape or volume stabilizer, metabolite, protein source, an agent for properly positioning the white blood cell subpopulation, an antioxidant, a debris reducer or a mixture thereof.

Other Control Ingredients

The simulated nucleated red blood cells prepared in accordance with the method disclosed herein may be used alone or with one or more other control ingredients. The control ingredients may be part of a kit in which one or more of the components for simulating a component of whole blood is provided separately (by itself or with another component) from the nucleated red blood cell component, such as a component for simulating a reticulocyte, being provided separately from the simulated nucleated red blood cell component.

Thus, the present simulated nucleated red blood cell components may be used to make a control composition or kit including one or more additional ingredients selected from a reticulocyte component; b) a white blood cell component; c) a red blood cell component; d) a nucleated red blood cell component; e) a platelet component; or f) a reticulated platelet component, preferably being mixed in a suitable isotonic suspension medium. Such a control or components thereof may be prepared in accordance with the teachings of U.S. Pat. Nos. 4,436,821; 5,008,201; 5,270,208; 5,262,327; 5,432,089; 6,200,500; 6,221,668, all of which are hereby incorporated by reference. Additional controls may be prepared in accordance with the subject matter set forth in U.S. Pat. Nos. 5,529,933; 5,994,139; 5,858,790; or 6,187,590, all of which are hereby incorporated by reference.

Optionally, for use in a control for attaining a 3 or 5 part differential of white blood cells, the control may contain a lipoprotein. While BSA in any diluent present improves the white blood cell position on the scattergram, lipoprotein may be used in an amount effective to provide a scattergram that represents whole blood, including the proper positioning of the five subpopulations of white blood cells. See, e.g., U.S. Pat. Nos. 5,270,208 and 5,262,327 incorporated by reference. By way of illustration, a lipoprotein source, preferably one consisting essentially of high-density lipoprotein (i.e., HDL) is added at about 0.5 to about 8.0% by volume of the control, and more preferably at about 100–175 mg/dl to the control composition and a-Tocopherol is further added to the lipoprotein source to reduce peroxides produced by the oxidation of the lipoproteins. An example of a suitable commercially available form of lipoprotein is SUPER-TRATE (available from Bayer). It will be appreciated that treatment with the lipoprotein may take place by adding the lipoprotein to a suspension medium for the control, it may take place by a pretreatment outside of the suspension medium, or a combination thereof.

Examples of commercially available media into which the nucleated red blood cell component of the present invention may be added include the STAK CHEX® product available commercially from Streck Laboratories. In another example, 5C™ control, from BeckmanCoulter is employed in combination with the nucleated red blood cell component of the present invention.

In another embodiment, the cells are suspended in a suitable isotonic wash solution, such as described herein.

One or a combination of more than one other agents may also be included in the control or provided along with the control. For example, in one embodiment, the component for simulating a nucleated red blood cell component is provided in a control or kit that also includes an absorbance agent (e.g., a dye or stain with a red color such as, without limitation, monoazo monochlorotriazinyl dyes, such as Cibacron Brilliant Red 3B-A, pyrimidinyl dyes, such as Procion Brilliant Red HE-7B; Poncau 3R Red Dye (Cl 16155); and FD&C Red #40) for simulating a predetermined hemoglobin concentration, as discussed in U.S. Pat. No. 5,994,139, hereby incorporated by reference.

In another embodiment, a stabilizing agent may be employed for stabilizing the size of a blood cell component (i.e., analog) when the control product is subjected to temperature ranging from –15° C. to 45° C., as discussed in U.S. Pat. No. 5,994,139, hereby incorporated by reference. Examples of suitable stabilizing agents include salts, polyols, and dimethyl sulfoxide, e.g., an agent selected from glycerol, ethylene glycol and propylene glycol and mixtures thereof. The stabilizing agent may be used at any suitable concentration (e.g., in the volume percent range of about 5% to about 30%).

As discussed previously, in another embodiment, the nucleated red blood cell component of the present invention is combined with a white blood cell component (analogs prepared from red or white blood cells).

By way of example (without limitation), the white blood cell component may be prepared from a sample of whole blood in which white blood cells are fixed prior to lysing of the red blood cells (e.g., with a suitable lysing agent such as Ammonium Chloride Tris solution) to remove them from the whole blood. After red blood cell lysis, the white blood cells are again fixed for a period of at least about 1 hour, and more preferably about 4 to about 5 hours.

The fixative agent may be any suitable art disclosed fixative, including but not limited to those including an aldehyde, oxazolidine, alcohol, cyclic urea, or the like. Examples of particularly preferred fixatives include, without limitation, formaldehyde, glutaraldehyde, diazolidinyl urea (DU), imidazolidinyl urea (IDU), dimethylol urea, dimethylol-5,5-dimethylhydantoin, 2-bromo-2-nitropropane-1,3-diol; quaternary adamantine; -hydroxymethyl-1-aza3,7-dioxabicyclo (3.3.0)octane and 5-hydroxymethyl-1-aza-3,7-dioxabicyclo (3.3.0)octane and 5-hydroxypoly-methyleneoxy-methyl-1-aza-3,7-dioxabicyclo (3.3.0)octane, sodium hydroxymethyl glycinate, and mixtures thereof; and or the like.

Other fixatives may be used, such as those disclosed in U.S. Pat. Nos. 5,196,182; 5,262,327; 5,460,797; 5,811,099; 5,849,517; 6,221,668, and 5,529,933; 6,187,590; 6,187,590, all of which are hereby incorporated by reference. As will be appreciated from the above, if desired, the fixative may be selected for preserving one or more of the surface antigens present on the blood cells, for permitting stain or dyeing of the blood cells, or for enabling some other treatment of the cells before or during analysis by a hematology instrument.

Preferably the volume concentration ratios of fixative to cell ranges from about 1:100 to about 100:1, more preferably about 1:20 to about 20:1, and still more preferably it is about 1:10 to about 10:1. A highly preferred example is about 1:10.

The fixing preferably takes place for a suitable period of time, such as ranging from about 1 to about 10 hours, more preferably about 3 to about 7 hours and still more preferably about 4 to about 5 hours. Preferably the fixative agent is maintained at about room temperature, though higher or lower temperatures may be suitably employed.

Lysing or Fixing Omitted

In another embodiment of the present invention, a control is prepared in which one and, more preferably, all of the above discussed fixing and lysing steps are omitted altogether in the preparation of the nucleated red blood cell component. This is the approach that is particularly preferred if the simulated nucleated red blood cell component is prepared from an alligator red blood cell. In this approach, the cells are provided from their respective source (e.g., an alligator). They are washed with an isotonic wash solution in one or more washing steps. In one preferred embodiment, they are kept in such a solution while being maintained at a temperature of about 10 to about 40° C., and more preferably about 18 to about 30° C. for longer than about one hour, more preferably longer than about 3 hours and still more preferably longer than about 12 hours (e.g., about 22 to about 30 hours). The resulting cells are then suspended in a suitable medium (as discussed for example in the section herein entitled "Other Control Ingredients", optionally with one or a plurality of other simulated blood components, for use as a control.

Using Control

The following discusses examples of methods of using the control composition to determine the accuracy and reproducibility of the operation of a multi-parameter automated hematology instrument. By way of example, a multi-parameter automated hematology instrument, such as a Beckman Coulter Gen-S or LH-700 System (optionally employing ACCUCOUNT technology offered by BeckmanCoulter), the Abbott Cell-Dyn 4000 Hematology System, Bayer ADVIA 120, and the Sysmex XE2100 System, is provided, optionally with a slide preparation module. The claimed control composition is obtained or prepared, optionally to illustrate low, normal or high values of a blood cell component. The control optionally is refrigerated prior to use. If so, at the beginning of testing, the control composition is allowed to warm to room temperature for about fifteen minutes, mixed manually, and checked for resuspension of contents.

The control composition is prepared and analyzed by the same standard method as test samples which may be tested in batch quantities by the use of a suitable cassette having apertures for receiving test vials. After preparation, the control composition and test samples are analyzed by detecting the presence of or counting the population number of each subject component type with a multi-parameter automated hematology instrument, which will preferably yield a visual display of the data. In one embodiment the control of the present invention is provided in combination with a peripheral devices, such as a device for tracking samples and associating them with particular data, such as a bar-code scanner system. The control may also be provided in combination with a slide preparation kit, stain or dye-resistant labels, lytic reagents (e.g., containing a quaternary ammonium salt), blood diluents, or other like components used in a clinical laboratory setting.

The automated test instrument may employ technology that analyzes cell samples in view of simultaneous volume conductivity and light scatter measurements, or solely by light scatter. Ordinarily, a starting sample is employed in combination with suitable reagents (which may comprise a component of a kit) and physical agitation for lysing and cell measuring by way of flow cytometry.

Examples of the various analysis techniques that might be employed will be apparent by familiarity with the above identified commercially available instruments, as well as by reference to art-disclosed techniques discussed in U.S. Pat. Nos. 6,060,322 (discussing "mixing a blood cell sample containing reticulated cells with a reagent composition comprising a metachromatic dye and a sphering agent to form a suspension of cells; 6,232,125 (stating that "Light scattering characteristics of the leukocytes are determined within five different angular ranges, all being lower than 40 degrees"); 6,228,652 (discussing use of "single transducer for simultaneously measuring the DC volume, RF conductivity, light scattering and fluorescence characteristics of blood cells passing through a cell-interrogation zone"); 5,917,584 (discussing "differentiation and enumeration of nucleated red blood cells without using fluorescence"); 5,874,311 (discussing "measuring low angle light scatter signal detected in less than 10° to differentiate reticulocytes from other cell types") 5,874,310(discusses "exposing a blood cell sample to a reagent system to lyse mature red blood cells and subsequently analyzing nucleated red blood cells in a flow cell by optical analysis" and the use of "two angles of light scatter signals" such as "low angle light scatter signals detected in less than 10°"). Other techniques are also discussed in U.S. Pat. Nos. 5,858,790 and 6,187,590. Of course, by no means is the mode of sample testing limited to the above. As mentioned other principles may be used.

Thus, in one embodiment, the present invention contemplates a method of using a control including a nucleated red blood cell component including the steps of providing a control including a stabilized blood cell suitable for simulating a nucleated red blood cell. The control (which may be provided in a kit) may also have other components such as those described herein, such as a white blood cell component for simulating at least five subpopulations of white blood cells. In one preferred embodiment, though not required, the white blood cell component has been prepared from a red blood cell, a white blood cell, or a mixture thereof, at least one of which has been contacted with a lipoprotein.

A hematology analyzer is provided. Preferably the analyzer is also adapted for differentiating white blood cells and for analyzing a blood cell sample by light scatter, and more preferably by two angles of light scatter measurement, which may include a medium angle light scatter signal and a right-angle light scatter. Preferably both signals are less than about 10° (e.g., one light scatter angle is in the range of about 0 to about 4° and the other light scatter angle is in the range of about 3 to about 7°) to differentiate nucleated red blood cells from other cell types. The control is passed through the hematology analyzer at a suitable temperature (e.g., at a temperature in the range of about 18 to about 28° C., though higher or lower temperatures are also possible). Optionally, the detection of the simulated nucleated red blood cell is performed in the absence of a fluorescent stain or dye. In one embodiment, the control is passed though the instrument only a single time, in order to obtain a satisfactory result. In another embodiment, the control is repeatedly passed though the instrument to assure test integrity.

The results of the analysis, which will resemble that of whole blood, may then be analyzed and reported. For example, the respective population counts obtained from the analysis are compared either to known reference value for each component type in the control composition, or by comparison of the population counts for each component types in the test sample with the corresponding values of components in the control composition. Data relating to the measurement of components in control composition and test samples is collected, monitored, stored, compared and analyzed by electronic means, such as part of a system including a computer programmed with appropriate software and containing appropriate data file structure, and preferably coupled with one or more devices for outputting or storing the data (e.g., a monitor, a printer, an electronic data storage medium or the like).

The skilled artisan will appreciate that a number of the steps and ingredients have been disclosed by way of specific example, but that any of a number of alternative steps or ingredients at the suggested or different parameter or concentration, may be suitably substituted. Though the ingredients or steps have been, in certain instances, described by reference to a particular function or result, it should be appreciated that such discussion is presented without intending to be bound by theory. In some instances, the ingredient or step will perform a different or an additional function or achieve a different result, or multiple other ingredients or steps may be substituted to perform such function or achieve such result. Thus, there is no intention to be bound to the breadth of any specific illustrative step, parameter, ingredient or concentration, where it is apparent that others may be advantageously be employed in addition to or as a substitute.

The present invention is further illustrated by particular reference to the following Examples, it being understood that variations of the same may be made while still remaining within the scope of the invention.

EXAMPLE 1

In this Example, a nucleated red blood cell component is prepared for a control for an automated instrument, such as those employing the detection or characterization technology of the STK-S or GEN-S Instruments offered commercially by Beckman Coulter. The present Example makes use of blood obtained from a reptile, specifically an alligator. The blood is obtained from any suitable supplier, and is preferably provided in a suitable medium containing an anticoagulant, such as in an Alsevers anticoagulant.

The alligator cells are then washed in an isotonic wash solution having a pH of about 7.1 and an osmolarity of about 305–325 mOsm. The wash solution preferably includes one or more of a surfactant, an antibiotic, a preservative or other ingredients, such as illustrated by the following (expressed in approximate amounts) "Table of Illustrative Wash Solution Ingredients":

| Table of Illustrative Wash Solution Ingredients | |
|---|---|
| 40 mg % | Methyl Paraben |
| 300 mg % | Polyethylene Glycol-molecular weight 20,000 |
| 1675 mg % | Ethylenediaminetetraacetic Acid |
| 933 mg % | Magnesium Gluconate |
| 639 mg % | Sodium Phosphate Dibasic anhydrous |
| 25 mg % | Adenosine |
| 25 mg % | Inosine |
| 40 mg % | Neomycin Sulfate |
| 15 mg % | Chloramphenicol |

A portion of the alligator cells are left unfixed and will be employed in at least two of the controls prepared according to the present example. The remaining portion is fixed with an aldehyde fixative (e.g., formaldehyde, glutaraldehyde or a mixture thereof) in a suitable proportion (e.g., about 1:1). (e.g., about 0.01%–0.05% glutaraldehyde, 0.05% -0.1% formaldehyde, or mixtures thereof). The glutaraldehyde samples are fixed according to cell concentration, while the formaldehyde samples are fixed by volume. After contact with any aldehyde, the cells are placed in an isotonic wash solution (e.g., as described above) for 22–30 hours at a temperature ranging from about 18–30° C.

Each of the fixed cells (for each fixative type), the unfixed cells and a mixture of fixed and unfixed cells are then added to a diluent, such as a multi-parameter hematology control (e.g., STAK-CHEX®, from Streck Laboratories or 5C, from BeckmanCoulter), in a count of approximately 1.5–2.9×10³ cells per mm³, to thus form 3 sets controls (fixed, unfixed and mixture of fixed and unfixed). The resulting 3 sets of controls each indicate the presence of nucleated red blood cells when run through an automated hematology analyzer, such as the STK-S or GEN-S instruments available from BeckmanCoulter.

EXAMPLE 2

In this Example, a nucleated red blood cell component is prepared for a control for an automated instrument, such as those employing the detection or characterization technology of the CELL-DYN 4000 Instrument offered commercially by Abbott Laboratories. The present Example makes use of blood obtained from a reptile, specifically an alligator. The blood is obtained from any suitable supplier, and is preferably provided in a suitable medium containing an anticoagulant, such as in an Alsevers anticoagulant.

The alligator cells are then washed in an isotonic wash solution having a pH of about 7.1 and an osmolarity of about 305–325 mOsm. The wash solution preferably includes one or more of a surfactant, an antibiotic, a preservative or other ingredients, such as illustrated by the following (expressed in approximate amounts) "Table of Illustrative Wash Solution Ingredients":

| Table of Illustrative Wash Solution Ingredients | |
|---|---|
| 40 mg % | Methyl Paraben |
| 300 mg % | Polyethylene Glycol-molecular weight 20,000 |
| 1675 mg % | Ethylenediaminetetraacetic Acid |
| 933 mg % | Magnesium Gluconate |
| 639 mg % | Sodium Phosphate Dibasic anhydrous |
| 25 mg % | Adenosine |
| 25 mg % | Inosine |
| 40 mg % | Neomycin Sulfate |
| 15 mg % | Chloramphenicol |

One part by volume concentrated Alligator cells is treated with ten parts by volume of a lysing agent, such as approximately 7–9mg % Saponin, introduced into a suitable isotonic wash solution, such as describe previously. The cells are left in this solution for about 22–30 hours at 18–30° C. The resulting supernatant containing the released hemoglobin is removed and the lysed alligator cells are resuspended in an isotonic wash solution, such as that described previously. Though hemoglobin has been substantially removed from the cells, the cytoplasmic membrane is still substantially intact, surrounding the nucleus.

About 1 part by volume of concentrated, lysed alligator cells is fixed in an aldehyde fixative (e.g., in about ten parts of about 1 to about 5% formaldehyde) in the above isotonic wash solution. The cells are fixed in this solution for about 22–30 hours at about 18–30° C.

The fixative is then removed from the cells by resuspending the cells in an isotonic wash solution, such as described in the above discussion. The resulting fixed and lysed alligator cells are added to a suitable medium, such as a multi-parameter hematology control (e.g., Para 12 Plus Retics™, from Streck Laboratories, Inc. in which the white blood cell component is prepared with a step of fixing prior to lysis of red blood cell components, or the control described generally in the following Table of Illustrative Control Ingredients, also optionally including a reticulocyte analog) at a count approximating about 1.5–2.9×10³ (or approximately 10% of the white blood cell component population) of nucleated red blood cells per mm³ in the resulting control.

| Table of Illustrative Control Ingredients |
|---|
| -Unfixed red blood cells |
| -Human white blood cells that are suspended about 1 part phosphate buffered saline having an osm of about 280 and including about 0.2% EDTA and about 1 part phosphate buffered saline having an osm of about 280 and including about 0.2% EDTA and about 15% Nuosept 145, held at about 50° C. for about 6 days |
| -Human platelets that are treated in a solution of about 1:1 isotonic wash solution (described above) plus about .025% glutaraldehyde at about 22° C. for about 2 days |
| -About 0.03% Soybean protease inhibitor |
| -Diluent (as set forth in the "Table of Illustrative Diluent" of Example 3, plus about 50 mg % NaF and about 10 mg % Sulfasalazine) |

The resulting control indicates the presence of nucleated red blood cells when run through an automated hematology analyzer, such as the CELL-DYN 4000 from Abbott Laboratories.

EXAMPLE 3

In this Example, a nucleated red blood cell component is prepared for a control for an automated instrument, such as those employing the detection or characterization technology of the XE 2100 Hematology Instrument offered commercially by Sysmex. The present Example makes use of blood obtained from a fish, specifically a salmon. The blood is obtained from any suitable supplier, and is preferably provided in a suitable medium containing an anticoagulant, such as in an Alsevers anticoagulant.

The blood cells are washed into a suitable medium (e.g., having a pH of about 7.4 and an osmolarity of about 320–340 mOsm , such as Hanks' Balanced Salt Solution with Urea, having the following approximate composition:

| | |
|---|---|
| 18.5 mg % | Calcium Chloride Dihydrate |
| 9.8 mg % | Magnesium Sulfate Anhydrous |
| 40 mg % | Potassium Chloride |
| 6 mg % | Potassium Phosphate Monobasic Anhydrous |
| 4.9 mg % | Sodium Phosphate Dibasic Anhydrous |
| 100 mg % | Glucose |
| 35 mg % | Sodium Bicarbonate |
| 2 mg % | Antimicrobial |
| 250 mg % | Urea |
| 700 mg % | NaCl |

Salmon cells are then fixed 1:1 (by volume) with a suitable aldehyde fixative (e.g., about 0.3–1.5% formaldehyde) in a liquid medium as described above, such as the Hank's solution. The cells are fixed in this solution for about 22–30 hours at about 18–30° C. The fixative is then removed from the salmon cells by resuspending the cells in a suitable diluent, such as that having a pH of about 7.1 and an osmolarity of about 285–305 mOsm and including one or more of a surfactant, an antibiotic, a preservative or other ingredients, such as approximated in the following:

| Table of Illustrative Diluent | |
|---|---|
| 1173 mg % | Ethylenediaminetetraacetic Acid |
| 653 mg % | Magnesium Gluconate |
| 447 mg % | Sodium Phosphate Dibasic Anhydrous |
| 300 mg % | Polyethylene Glycol-molecular weight 20,000 |
| 25 mg % | Adenosine |
| 25 mg % | Inosine |
| 140 mg % | Sodium Hydroxide |
| 40 mg % | Methyl Paraben |
| 40 mg % | Neomycin Sulfate |
| 5 mg % | Sodium Fluoride |
| 1000 mg % | Glucose |
| 15 mg % | Chloramphenicol |

The resulting fixed and lysed salmon cells are added to a suitable medium, such as a multi-parameter hematology control (e.g., e-CHEX™ Control from Sysmex) at a count approximating about 1.5–2.9×10³ cells per mm³ in the resulting control. The resulting control indicates the presence of nucleated red blood cells when run through an automated hematology analyzer, such as the XE 2100 from Sysmex.

Like results are also obtained when the concentrations of the nucleated red blood cell component are varied to simulate normal, low or high values of the components.

Quantitative amounts of the nucleated red blood cell component may also be obtained with the above controls, on an instrument employing a detector suitable for counting.

While the above has been described in connection with simulation of human nucleated red blood cells, it should be appreciated that the invention may be modified within the scope of the present invention for achieving a simulation of nucleated red blood cells in mammals other than humans, or other animals. Thus, the present invention is not intended as limited to the use of the subject matter herein for clinical analysis of human blood, but may be extended as desired to a variety of veterinary or other applications where it is desired to simulate a nucleated cell.

The foregoing discussion discloses and describes merely exemplary embodiments of the present invention. One skilled in the art will readily recognize from such discussion and from the accompanying drawings and claims, that various changes, modifications and variations can be made therein without departing from the spirit and scope of the invention as defined in the following claims. All patents and other publications cited herein are expressly incorporated by reference.

What is claimed is:

1. A method of using a control including a nucleated red blood cell component comprising the steps of:
   a) providing a control including a stabilized blood cell suitable for simulating a nucleated red blood cell, the stabilized blood cell including a membrane enclosing a nucleus and wherein the cytoplasm of the stabilized blood cell has been substantially removed from within said membrane;
   b) providing a hematology analyzer for analyzing a blood cell sample by at least two angles of light scatter measurement to differentiate nucleated red blood cells from other cell types;
   c) passing the control through the hematology analyzer for detection of the simulated nucleated red blood cells;
   a
   d) reporting nucleated red blood cells in said control.

2. The method of claim 1, wherein a first angle of light scatter measurement is in the range of about 0 to about 4° and a second angle of light scatter measurement is in the range of about 4 to about 7°.

3. The method of claim 1, wherein the detection is performed in the absence of a fluorescent stain or dye.

4. The method of claim 1, wherein the passing step takes place at a temperature in the range of about 18 to about 28° C.

5. A method of using a control including a nucleated red blood cell component comprising the steps of:
   a) providing a control that is suitable for use for at least 3 days, including:
      i) a stabilized blood cell suitable for simulating a nucleated red blood cell, the stabilized blood cell including a membrane enclosing a nucleus and wherein the cytoplasm of the stabilized blood cell has been substantially removed from within said membrane;
      ii) a white blood cell component for simulating at least three subpopulations of white blood cells;
   b) providing a hematology analyzer differentiating white blood cells and for analyzing a blood cell sample by at least one angle of light scatter measurement to differentiate nucleated red blood cells from other cell types;
   c) passing the control through the hematology analyzer for detection of the simulated nucleated red blood cells and subpopulations of white blood cells;
   d) reporting simulated white blood cells in the control; and
   e) reporting simulated nucleated red blood cells in the control.

6. The method of claim 5, wherein a first angle of light scatter measurement is in the range of about 0 to about 4° and a second angle of light scatter measurement is in the range of about 4 to about 7°.

7. The method of claim 5, wherein the detection is performed in the absence of a fluorescent stain or dye.

8. The method of claim 5, wherein the passing step takes place at a temperature in the range of about 18 to about 28° C.

9. A method of using a control including a nucleated red blood cell component comprising the steps of:
   a) providing a control that is suitable for use for at least 45 days, including:
      i) a stabilized blood cell suitable for simulating a nucleated red blood cell the stabilized blood cell including a membrane enclosing a nucleus and wherein the cytoplasm of the stabilized blood cell has been substantially removed from within said membrane;
      ii) a white blood cell component for simulating at least five subpopulations of white blood cells, the white blood cell component having been prepared from a red blood cell, a white blood cell, or a mixture thereof, at least one of which has been contacted with a lipoprotein;
   b) providing a hematology analyzer for differentiating white blood cells and for analyzing a blood cell sample by at least two angles of light scatter measurement both being less than about 10° to differentiate nucleated red blood cells from other cell types;
   c) passing the control through the hematology analyzer at a temperature in the range of about 18 to about 28° C. for detection of the simulated nucleated red blood cells and subpopulations of white blood cells;
   d) reporting simulated white blood cells in the control; and
   e) reporting simulated nucleated red blood cells in the control.

10. The method of claim 9, wherein a first light scatter angle is in the range of about 0 to about 4° and a second light scatter angle is in the range of about 3 to 7°.

11. The method of claim 9, wherein the control is passed only a single time through the hematology analyzer for assuring a reliable result.

12. The method of claim 9, wherein the stabilized blood cell suitable for simulating a nucleated red blood cell is unfixed.

13. A method of using a control including a nucleated red blood cell component comprising the steps of:
   a) providing a control including a stabilized blood cell suitable for simulating a nucleated red blood cell, the blood cell including a membrane enclosing a nucleus and wherein the stabilized blood cell is selected from the group consisting of reptile blood, fish blood and mixtures thereof;
   b) providing a hematology analyzer or analyzing a blood cell sample by at least two angles of light scatter measurement to differentiate nucleated red blood cells from other cell types;
   c) passing the control through the hematology analyzer for detection of the simulated nucleated red blood cells;
   d) reporting nucleated red blood cells in said control.

14. The method of claim 13, wherein the stabilized blood cell suitable for simulating a nucleated red blood cell is unfixed.

* * * * *

UNITED STATES PATENT AND TRADEMARK OFFICE
CERTIFICATE OF CORRECTION

PATENT NO. : 6,653,137 B2
DATED : November 25, 2003
INVENTOR(S) : Wayne L. Ryan

It is certified that error appears in the above-identified patent and that said Letters Patent is hereby corrected as shown below:

Column 12,
Line 66, delete "a" and insert -- and --.

Column 13,
Line 46, after "red blood cell" insert -- , --.

Column 14,
Line 9, after "measurement" insert -- , --.
Line 10, after "10°" insert -- , --.
Line 15, delete "C." and insert -- C --.
Line 34, before "blood" insert -- stabilized --.
Line 39, delete "or" and insert -- for --.
Line 44, after "cells;" insert -- and --.

Signed and Sealed this

Fourteenth Day of September, 2004

JON W. DUDAS
*Director of the United States Patent and Trademark Office*